United States Patent [19]

Dalkiaer

[11] Patent Number: 4,917,762
[45] Date of Patent: Apr. 17, 1990

[54] PROCESS FOR MANUFACTURING A LIQUID ABSORBING PAD

[76] Inventor: Peter Dalkiaer, Kyhnsvej 4, DK-2930 Klampenborg, Denmark

[21] Appl. No.: 220,940

[22] Filed: Jun. 23, 1988

Related U.S. Application Data

[63] Continuation of Ser. No. 829,641, filed as PCT DK85/00090 on Oct. 1, 1985, published as WO86/02116 on Apr. 10, 1986, abandoned.

[30] Foreign Application Priority Data

Oct. 1, 1984 [DK] Denmark .............................. 4700/84

[51] Int. Cl.$^4$ ............................................... D21B 1/32
[52] U.S. Cl. ........................................ 162/5; 162/100; 162/158; 162/201; 241/28; 264/115; 264/116; 264/121
[58] Field of Search ...................... 241/28; 162/5, 100, 162/158, 147, 182, 179, 201, 4; 264/115, 116, 121

[56] References Cited

U.S. PATENT DOCUMENTS

| | | | |
|---|---|---|---|
| 3,081,316 | 3/1978 | Aberg et al. | 162/4 |
| 3,395,708 | 8/1968 | Hervey et al. | 162/158 |
| 3,773,613 | 11/1973 | Lee et al. | 162/100 |
| 4,065,347 | 12/1977 | Aberg et al. | 162/100 |
| 4,444,830 | 4/1984 | Erickson | 241/28 |

FOREIGN PATENT DOCUMENTS 940250 10/1963 United Kingdom ................... 162/5

Primary Examiner—Peter Chin
Attorney, Agent, or Firm—Fleit, Jacobson, Cohn, Price, Holman & Stern

[57] ABSTRACT

A liquid absorbing pad, in particular for use in hygiene articles and sanitary products, such as diapers, bed pads, sanitary napkins, pads for incontinence, panty shields, nursing pads or the like, is produced in a dry and direct process on the basis of wet-strength and/or coated paper waste, especially originating from the production of food packages, milk carton packages, deep-freeze packages, disposable tableware and the like. The waste is cut and defibrated, and during the defibration or just before it a maximum of 25% by volume, based on the volume of the paper waste, of a mixture of water and a surfactant is added to reestablish the absorption capacity of the fibres. Starting materials otherwise difficult to process can thus be used in a dry and direct process.

8 Claims, No Drawings

PROCESS FOR MANUFACTURING A LIQUID ABSORBING PAD

This application is a continuation of application Ser. No. 829,641, filed as PCT DK85/00090 on Oct. 1, 1985, published as WO86/02116 on Apr. 10, 1986, now abandoned.

The present invention concerns a process for manufacturing a liquid absorbing pad, in particular for use in soft hygiene articles and sanitary products, such as diapers, bed pads, bandages, sanitary napkins, different "pads" in connection with incontinence, panty shields, nursing pads, and similar products, but useful in any situation where rapid and reliable absorption of liquid is desired, e.g. in the packaging and transport of liquid releasing articles, such as frozen goods. The present liquid absorbing pad is manufactured on the basis of cellulose pulp, defibrated in a dry process and formed to the desired product. The process of the invention is characterized by using as cellulose pulp wet strength and/or coated waste paper cut in suitable sizes before defibration, and adding during the defibration or just before it a mixture of water and a surfactant to the waste material in order to reestablish the absorption capacity of the fibres.

The waste paper starting material has its origin from the production of food packages, milk carton packages, deep-freeze packages, disposable tableware and the like. This material may appear in the shape of strips, cuttings, sheets, rolls, balls, etc. in a loose or a compact form. The material may be coated with wax, plastics, foil and the like, and it may be printed either above or under the coating.

The Danish Patent Specification 127 258 describes a process for producing a pad of soft and fibrous wood paper mass used especially in sanitary products. In this process specified surfactants are added to the wet cellulose pulp, which is then pressed, dried and formed to a sheet.

This known process relies upon treatment of the cellulose mass with a surfactant while the mass is in the wood pulp stage, primarily in order to achieve a loose binding of the fibres, when the produced sheet of paper is subsequently to be defibrated in the production of sanitary products.

In the process of the invention the paper waste material is processed directly and without a wet pulp process, and the surfactant is added just before or during the defibration process in order to reestablish the absorption capacity of the fibres.

In consequence of the increasing quantities of paper waste in the industrialized countries, it is desirable to use this waste material in the production of new products, for economic as well as for environmental reasons. In fact, paper waste is greatly reused today.

However, not all types of paper waste can be recycled with the same ease. One type of paper waste which has until now been considered less suitable for reuse due to the involved complexity and costs, is waste paper from the production of coated food packages and the like. Such packages are often coated with wax, plastics, foils and the like and will at the same time have wet-strength. This means that such types of paper waste are very difficult to decompose and to process to other paper products.

The U.S. Patent Specification 2 394 273 discloses a process for decomposition of wet-strength paper for reuse. In this process, resin-impregnated waste paper is dissolved by heating an acid (pH <5) 0.6% suspension of the waste material to a temperature of about 37° to 100° C., and mechanical disintegration is then performed.

The U.S. Patent Specification 2 488 515 describes a process for treating waste wax paper, wherein the waste paper is suspended in water heated to a temperature sufficiently high to melt the wax. The molten wax, which is fixed to the fibres, is released from these by addition of a cationic surfactant selected from among amino amides and salts thereof. The temperature required to melt the wax is typically 50° to 70° C.

A more drastic method is described in the U.S. Patent Specification 3 425 897, in which wet-strength waste paper is decomposed and dissolved by cooking alkaline suspensions of the waste under pressure for up to five hours with a further alkaline treatment under milder conditions.

These known methods for decomposing wet-strength paper waste to re-create the paper fibres thus do not make it obvious to use this type of waste as a raw material in a direct production of other paper products. As will be seen, the known methods generally demand long heating of the paper suspensions, and since these are rather strongly diluted, the consumption of energy will be considerable. Further, the purpose of these known methods is only to convert the paper fibres, primarily through a chemical treatment. The defibering method in the invention, however, is essentially a mechanical one.

More particularly, it has now surprisingly been found that liquid absorbing pads, in particular for use in soft hygiene articles and sanitary products, such as diapers, etc., on the basis of wet-strength and/or coated paper waste, including cuttings from milk carton packages, can be manufactured in a direct and dry process without adding any heat. This process is performed by initially chopping or cutting the paper waste in suitable sizes. The cut material is then metered (volumetric metering) and is passed on to the very defibration, which may take place in a hammer mill, a refiner or in other suitable mechanical units.

During or just before the defibration, a mixture of water and a surfactant, preferably an anionic surfactant, is added to the waste in order to reestablish the absorption capacity of the fibres.

The quantity of water and surfactant does not exceed 20% by volume of the mixture of waste and liquid. This addition of liquid is decisive for the fibre absorption capacity recovery. Products produced in this way have an excellent liquid absorption capacity, whereas products produced without the addition of water and surfactant literally do not absorb liquid.

The surfactant constitutes from 0.1 to 20% by volume of the mixture of water and surfactant. In the production of hygiene articles a maximum of up to 10% by volume is preferably used.

After the defibration the product is formed in a manner known per se to provide absorbing products for any field of use, such as diapers, bed pads, bandages, sanitary napkins, various pads in connection with incontinence, panty shields, nursing pads and other absorbing products with excellent absorption capacity. The defibrated product, which may be more or less compact, can also be formed for instance as balls or rolls for later use as a starting material in processes known per se for absorbing products, such as hygiene articles and sanitary products.

The surfactant can for instance be an anionic agent. Such anionic agents include for instance Aerosol®OT 75 from Cyanamid B.V. in Holland which is a 75% solution of sodium dioctyl sulfosuccinate, or Tensid 7478 from Berol Kemi in Sweden, which is an anionic tenside of the sulfosuccinate diester type based on 2-ethyl hexanol (Na salt). But other surfactants can also be used, including non-ionic and cationic surfactants. Among the cationic surfactants may be mentioned Berocell®584 from Berol Kemi in Sweden. Other long-chained cationic surfactants may be used as well, in particular those having at least 12 carbon atoms in at least one alkyl chain.

The invention is illustrated more fully by the following working example.

EXAMPLE

The starting material is cuttings from the production of milk carton packages, present in sizes with a width of 1 to 3 cm and a length of 10 to 30 cm. The material is pre-cut to more uniform pieces, which are then transported to an intermediate store (silo), from which the material, after coarse metering (worm) and fine metering (brush rollers over a vacuum deck) is conveyed to the defibration which is performed in a Sunds disc refiner.

At the same time the material is admixed with a mixture of a surfactant (Aerosol®OT 75) and water in which the concentration of the surfactant is 1.35% by volume.

The defibrated fibres are then passed to a diaper machine in which formation of a fibre mat and subsequent "wrapping" of the fibre mass are performed in a manner known per se.

This production is continuous with a normal amount per minute varying between 10 and 14 kg of raw materials.

The produced product—a rectangular diaper with a weight of 44 g—has an overall absorption capacity of 260 g of liquid, which, excluding the amount of inactive raw material corresponding to 12 to 15%, has an absorption capacity (g/g) of approximately the same level as the corresponding, commercially available products.

I claim:

1. A process for manufacturing a defibrated material for use as a liquid absorbing pad in soft hygiene articles and sanitary products, comprising the steps of:
   providing coated or uncoated wet-strength container board or packaging paper as cellulose pulp;
   cutting said cellulose pulp in suitable sizes for defibration;
   defibrating said cellulose pulp by a dry process; and
   adding a mixture of water and a surfactant to the cut cellulose pulp during or just before the defibration step to reestablish the abosrption capacity of the cellulose pulp fibres, said mixture of water and surfactant comprising a maximum of 20% by volume of the resultant cellulose pulp, water and surfactant mixture, thereby producing an absorbent defibrated material.

2. A process as claimed in claim 1 comprising the additional step of forming the defibrated material into diapers, bed pads, sanitary napkins, pads in connection with incontinence, panty shields, nursing pads and similar hygiene articles.

3. A process as claimed in claim 1, comprising the additional step of forming the defibrated material into rolls, sheets, balls, blocks or the like, suitable for use as a starting material in a process for producing soft hygiene articles.

4. A process as claimed in claim 1, wherein the paper waste used as cellulose pulp has its origin from the production of food packages, milk carton packages and deep-freeze packages, or disposable tableware.

5. A process as claimed in claim 4, wherein the waste is present in the shape of strips, cuttings, sheets, rolls, balls or the like either in a loose or a compact form.

6. A process as claimed in claim 1, wherein the concentration of the surfactant is 0.1 to 20% by volume, based on the mixture of water and surfactant.

7. A process according to claim 6, wherein the concentration of the surfactant is 0.1 to 10% by volume, based on the mixture of water and surfactant.

8. A process according to claim 6, wherein the concentration of the surfactant is 0.1 to 5% by volume, based on the mixture of water and surfactant.

* * * * *